US009135401B2

(12) United States Patent
Zhan et al.

(10) Patent No.: US 9,135,401 B2
(45) Date of Patent: Sep. 15, 2015

(54) INFORMATION-THEORETIC VIEW OF THE SCHEDULING PROBLEM IN WHOLE-BODY COMPUTER AIDED DETECTION/DIAGNOSIS (CAD)

(75) Inventors: Yiqiang Zhan, Berwyn, PA (US); Xiang Zhou, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1766 days.

(21) Appl. No.: 12/181,375

(22) Filed: Jul. 29, 2008

(65) Prior Publication Data

US 2009/0037919 A1    Feb. 5, 2009

Related U.S. Application Data

(60) Provisional application No. 60/953,554, filed on Aug. 2, 2007.

(51) Int. Cl.
*G06F 19/00* (2011.01)
(52) U.S. Cl.
CPC .................................. *G06F 19/345* (2013.01)
(58) Field of Classification Search
USPC ................... 600/407, 410, 411, 416; 718/103
See application file for complete search history.

(56) References Cited

U.S. PATENT DOCUMENTS

2007/0167718 A1 * 7/2007 Kaufman et al. ............. 600/407

OTHER PUBLICATIONS

Zhou et al, Conditional Feature Sensitivity: A Unifying View on Active Recognition and Feature Selection, 2003, IEEE, 2-Volume Set.*
Visvikis et al, Impact of technology on the utilisation of positron emission tomography in lymphoma: current and future perspectives, May 13, 2003, Springer-Veriag, vol. 30, Suppliment 1, S106-S116.*
Zhan et al, "An Information Theoretic View of the Scheduling Problem in Whole-Body CAD", Proc. SPIE, vol. 6915, 691515 (2008).
Logothetis et al., "On sensor scheduling via information theoretic criteria", American Control Conference, 1999, Proceedings of the 1999 San Diego, CA, Jun. 2-4, 1999, Piscataway, NJ, IEEE, vol. 4, Jun. 2, 1999, pp. 2402-2406.
Brown et al., "Information theoretic sensor data selection for active object recognition and state estimation", IEEE Transactions on Pattern Analysis and Machine Intelligence, IEEE Service Center, Los Alamitos, CA, vol. 24, No. 1, Feb. 1, 2002, pp. 145-157.
Wells et al., "Multi-modal volume registration by maximization of mutual information", Medical Image Analysis, Oxford University Press, Oxford, GB, vol. 1, No. 1, Jan. 1, 1996, pp. 35-51.

(Continued)

*Primary Examiner* — Rochelle Turchen
(74) *Attorney, Agent, or Firm* — Peter R. Withstandley

(57) ABSTRACT

A method for automatically scheduling tasks in whole-body computer aided detection/diagnosis (CAD), including: (a) receiving a plurality of tasks to be executed by a whole-body CAD system; (b) identifying a task to be executed, wherein the task to be executed has an expected information gain that is greater than that of each of the other tasks; (c) executing the task with the greatest expected information gain and removing the executed task from further analysis; and (d) repeating steps (b) and (c) for the remaining tasks.

15 Claims, 8 Drawing Sheets

(56) References Cited

OTHER PUBLICATIONS

Zhan et al., "An information theoretic view of the scheduling problem in whole-body CAD", Proceedings of the SPIE—The International Society for Optical Engineering, vol. 6915, No. 1, Mar. 6, 2008, pp. 691515-1-691515-10.

Zhan et al., "Active Scheduling of Organ Detection and Segmentation in Whole-Body Medical Images", Medical Image Computing and Computer-Assisted Intervention A MICCAI 2008; (Lecture notes in Computer Science), vol. 5241, Sep. 2008, pp. 313-321.

* cited by examiner

INFORMATION-THEORETIC VIEW OF THE SCHEDULING PROBLEM IN WHOLE-BODY COMPUTER AIDED DETECTION/DIAGNOSIS (CAD)

CROSS-REFERENCE TO RELATED APPLICATION

This application claims the benefit of U.S. Provisional Application No. 60/953,554, filed Aug. 2, 2007, the disclosure of which is incorporated by reference herein in its entirety.

BACKGROUND OF THE INVENTION

1. Technical Field

The present invention relates to whole-body computer aided detection/diagnosis (CAD) scheduling.

2. Discussion of the Related Art

Recently, emerging whole-body imaging technology has paved the way to scale up medical image-based diagnosis to a whole-body level. Whole-body computed tomography (CT)/positron emission tomography (PET)/magnetic resonance (MR) scanning help radiologists in various diagnostic problems, including assessment of cancer metastasis in lymph (D. Visvikis and P. J. Ell, "Impact of technology on the utilisation of positron emission tomography in lymphoma: current and future perspectives", European Journal of Nuclear Medicine and Molecular Imaging 30, pp. 1619-1670, 2002) or bones (M. Niitsu and T. Takeda, "Solitary hot spots in the ribs on bone scan: value of thin-section reformatted computed tomography to exclude radiography-negative fractures", J Compu Assis Tomogr. 27, pp. 469-474, 2003), evaluation of the extent and distribution of polymyositis (M. O'Connell, T. Powell, D. Brennan, T. Lynch, C. McCarthy and S. Eustace, "Whole-body mr imaging in the diagnosis of polymyositis", AJR Am J Roentgenol. 179, pp. 967-971, 2002), and detection of ankylosing spondylitis (U. Weber, C. W. Pfirrmann, R. O. Kissling and J. H. M. Zanetti, "Whole body mr imaging in ankylosing spondylitis: a descriptive pilot study in patients with suspected early and active confirmed ankylosing spondylitis", BMC musculoskeletal disorders 8, 2007). However, the vast amount of image data in whole-body scans (more than 400 slices) makes the detection of potential disease a burdensome and tedious task for radiologists. Accordingly, CAD becomes more desirable for whole-body scans to provide a useful "second opinion" for radiologists.

As a whole-body CAD system often involves multiple organs that have strong anatomical or functional dependency, it is actually a multi-task system where different tasks are highly dependent. One way to exploit task dependency is to execute the tasks in a schedule such that outputs of some tasks can be used to guide the others. For example, the relatively easy task of femoral head localization in CT (bone is very bright in CT) will facilitate a quick and accurate localization of the iliac bifurcation of the aorta, which in turn greatly helps the detection and identification of abdominal lymph node clusters (see FIG. 1). However, while the idea of executing multiple tasks of whole-body CAD in a particular order has been accepted, whole-body CAD is usually scheduled heuristically and the scheduling method (how to determine the schedule?) has not been well investigated.

In the past decades, scheduling topics have been extensively studied in the areas of operation research (P. Brucker, "Scheduling algorithms", 4th edition, Springer, 2004) and theoretical computer science (K. Pruhs, J. Sgall and E. Torng, Handbook of Scheduling: Algorithms, Models, and Performance Analysis, CRC Press, 2003). Many scheduling rules/methods were proposed to deal with scheduling problems in various applications, including manufacturing, service industries, transportation and practical computer systems, etc. While earlier studies (J. E. Kelley, "Critical-path planning and scheduling: Mathematical basis", Operations Research 9, pp. 296-320, 1961) mainly focus on deterministic systems, more researchers have recently moved to flexible and stochastic systems. In Nam's work (I. hyun Nam, "Dynamic scheduling for a flexible processing network", Operations Research 49, pp. 305-315, 2001), the scheduling policies for flexible systems were investigated. This work analyzed an open processing network model with discretionary routing and showed, in general, that unbalanced workload routing with priority sequencing gives better performance than a balanced one. Chou et al. (M. C. Chou, H. Liu, M. Queyranne and D. Simchi-Levi, "On the asymptotic optimality of a simple on-line algorithm for the stochastic single-machine weighted completion time problem and its extensions", Operations Research 54, pp. 464-474, 2006) studied a stochastic single machine problem, where the actual processing time of tasks are not known until processing is complete. They proved that when task weights and processing times are bounded and task processing times are mutually independent random variables, a weighted shortest expected processing time among available jobs (WSEPTA) heuristic is asymptotically optimal for the single-machine problem. Cres et al. (H. Cres and H. Moulin, "Scheduling with opting out: Improving upon random priority", Operations Research 49, pp. 565-577, 2001) studied the problem where agents can opt out. They showed that the familiar random priority (RP) mechanism can be improved upon by another mechanism dubbed probabilistic serial (PS). Gilland et al. (W. G. Gilland, "Effective sequencing rules for closed manufacturing networks", Operations Research 49, pp. 759-770, 2001) developed a method for determining sequencing policies to effectively control a multi-station closed queuing network. Here, a Brownian control problem that approximates the original queuing network is formulated and used to develop a dynamic sequencing policy that seeks to prevent idleness, unless the system is at a face of a workload imbalance polytope that arises in the Brownian formulation.

Although the aforementioned scheduling problems have been successfully applied to various industrial areas, they have limitations in CAD scheduling, due to the unique characteristics of whole-body CAD summarized as follows.

First, the schedule of whole-body CAD is highly flexible. The accuracy and speed of CAD systems, however, is significantly different with different schedules. Second, due to missing data, artifacts or diseases, the scheduler of whole-body CAD must be an active one. In other words, the scheduling must be adaptive to the specific patient data at the runtime. Refer to the previous example, in general cases, the detector of iliac bifurcation should be fired next to the "femoral head localization". However, for a patient who has an artificial mental femoral head, the femoral head detector might not detect it correctly and usually return a result with very low confidence. In this situation, instead of firing the "iliac bifurcation detector", the scheduler should trigger the detectors of other organs, e.g., kidneys, which can be localized accurately without the inference of femoral heads. Third, multiple tasks are often statistically dependent. Refer to the previous example, "iliac bifurcation localization" is statistically dependent on "femoral heads localization", as the relative locations of the iliac bifurcation with respect to the femoral heads are not deterministic. Finally, the outcome of tasks usually embeds uncertainties. Since tasks are mutually dependent, uncertainties in one task might influence the speed and accuracy of other tasks.

Accordingly, there exists a need for scheduling tasks in whole-body CAD at high speeds and with great accuracy.

SUMMARY OF THE INVENTION

In an exemplary embodiment of the present invention, a method for automatically scheduling tasks in whole-body computer aided detection diagnosis (CAD), comprises: (a) receiving a plurality of tasks to be executed by a whole-body CAD system; (b) identifying a task to be executed, wherein the task to be executed has an expected information gain that is greater than that of each of the other tasks; (c) executing the task with the greatest expected information gain and removing the executed task from further analysis; and (d) repeating steps (b) and (c) for the remaining tasks.

The plurality of tasks comprises a plurality of organs or anatomical structures to be located in a plurality of whole-body scans. The whole body scans comprise computed tomography (CT), positron emission tomography (PET) or magnetic resonance (MR) scans.

The expected information gain is represented by the following equation:

$$IG_y = \sum_i \left( H(x_i \mid y \in \Psi) - \int_{y \in \Psi} H(x_i \mid y \in \Phi) p(y) dy \right),$$

wherein $H(x_i|y \in \Psi)$ is a conditional entropy before executing the task and $H(x_i|y \in \Phi)$ is a conditional entropy after executing the task, $x_i$ is a goal of the task, y is an outcome after executing the task, $\Psi$ is a distribution of the outcome before executing the task and $\Phi$ is a distribution of the outcome after executing the task.

A task that has the greatest information gain includes a stronger shrink of the support from $\Psi$ to $\Phi$ than other tasks and a strong correlation of y* over $x_i$ after executing the task than other executed tasks.

A Monte Carlo simulation method is used to calculate the conditional entropies, evaluate the expected information gain of each of the tasks and pick the task that has the greatest expected information gain as the task to be executed.

In an exemplary embodiment of the present invention, a system for automatically scheduling tasks in whole-body CAD, comprises: a memory device for storing a program; a processor in communication with the memory device, the processor operative with the program to: (a) receive a plurality of tasks to be executed by a whole-body CAD system; (b) identify a task to be executed, wherein the task to be executed has an expected information gain that is greater than that of each of the other tasks; (c) execute the task with the greatest expected information gain and remove the executed task from further analysis; and (d) repeat steps (b) and (c) for the remaining tasks.

The plurality of tasks comprises a plurality of organs or anatomical structures to be located in a plurality of whole-body scans. The whole body scans comprise CT, PET or MR scans.

The expected information gain is represented by the following equation:

$$IG_y = \sum_i \left( H(x_i \mid y \in \Psi) - \int_{y \in \Psi} H(x_i \mid y \in \Phi) p(y) dy \right),$$

wherein $H(x_i|y \in \Psi)$ is a conditional entropy before executing the task and $H(x_i|y \in \Phi)$ is a conditional entropy after executing the task, $x_i$ is a goal of the task, y is an outcome after executing the task, $\Psi$ is a distribution of the outcome before executing the task and $\Phi$ is a distribution of the outcome after executing the task.

A task that has the greatest information gain includes a stronger shrink of the support from $\Psi$ to $\Phi$ than other tasks and a strong correlation of y* over $x_i$ after executing the task than other executed tasks.

A Monte Carlo simulation method is used to calculate the conditional entropies, evaluate the expected information gain of each of the tasks and pick the task that has the greatest expected information gain as the task to be executed.

In an exemplary embodiment of the present invention, a computer readable medium tangibly embodying a program of instructions executable by a processor to perform method steps for automatically scheduling tasks in whole-body CAD, the method steps comprising: (a) receiving a plurality of tasks to be executed by a whole-body CAD system; (b) identifying a task to be executed, wherein the task to be executed has an expected information gain that is greater than that of each of the other tasks; (c) executing the task with the greatest expected information gain and removing the executed task from further analysis; and (d) repeating steps (b) and (c) for the remaining tasks.

The plurality of tasks comprises a plurality of organs or anatomical structures to be located in a plurality of whole-body scans. The whole body scans comprise CT, PET or MR scans.

The expected information gain is represented by the following equation:

$$IG_y = \sum_i \left( H(x_i \mid y \in \Psi) - \int_{y \in \Psi} H(x_i \mid y \in \Phi) p(y) dy \right),$$

wherein $H(x_i|y \in \Psi)$ is a conditional entropy before executing the task and $H(x_i|y \in \Phi)$ is a conditional entropy after executing the task, $x_i$ is a goal of the task, y is an outcome after executing the task, $\Psi$ is a distribution of the outcome before executing the task and $\Phi$ is a distribution of the outcome after executing the task.

A task that has the greatest information gain includes a stronger shrink of the support from $\Psi$ to $\Phi$ than other tasks and a strong correlation of y* over $x_i$ after executing the task than other executed tasks.

A Monte Carlo simulation method is used to calculate the conditional entropies, evaluate the expected information gain of each of the tasks and pick the task that has the greatest expected information gain as the task to be executed.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention

DETAILED DESCRIPTION OF EXEMPLARY EMBODIMENTS

1. Introduction

In accordance with an exemplary embodiment of the present invention, we study the scheduling problem of whole-body computer aided detection/diagnosis (CAD) from an information theoretic view. In this framework, multiple tasks of whole-body CAD are modeled as a set of measurements that aim to achieve diagnostic information from medical images. The principle is to schedule tasks in an order that is optimal in an information-theoretic sense. More specifically, we explore the gauge of information gain to define the scheduling criterion. Based on this criterion, a sequential decision making process is employed to schedule tasks in whole-body CAD. There are two major advantages of our method. First, various probabilistic factors that influence the performance and speed of whole-body CAD are incorporated in the scheduling criterion. Therefore, the scheduled system is able to achieve more accurate results with less computational cost. Second, in our scheduling method, the next task is always determined based on current system status. In other words, the whole-body CAD is scheduled in an active way and thus is adaptive to different patient images.

Figure 1:
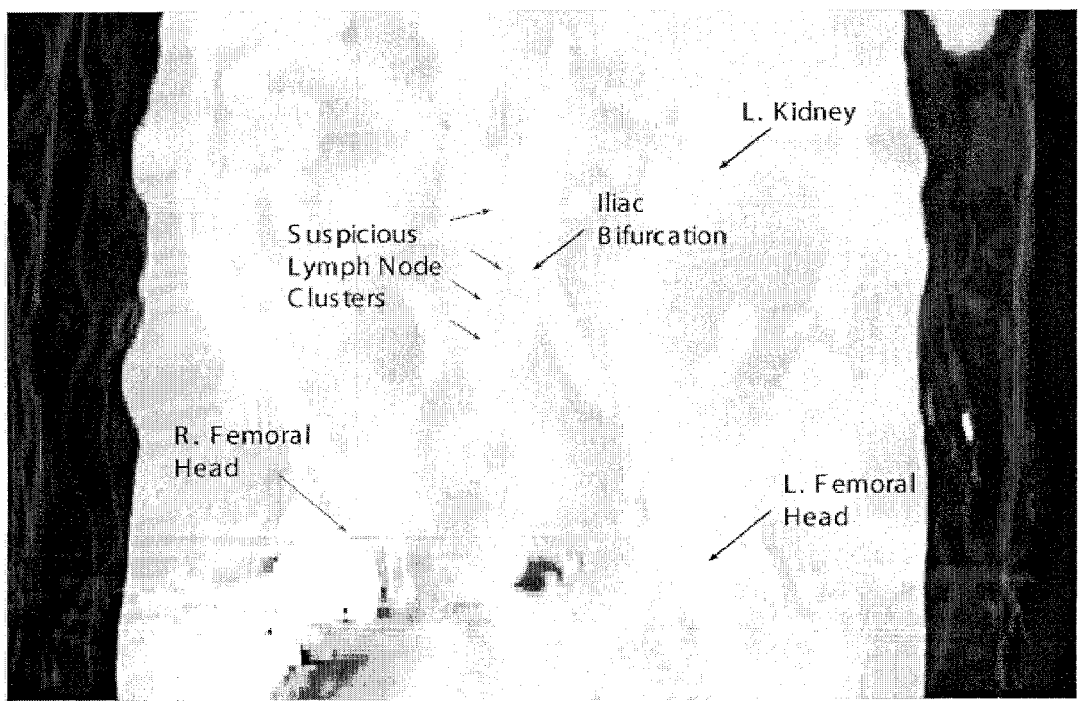
FIG. 1 is a representative computed tomography (CT) image.
Figure 2:
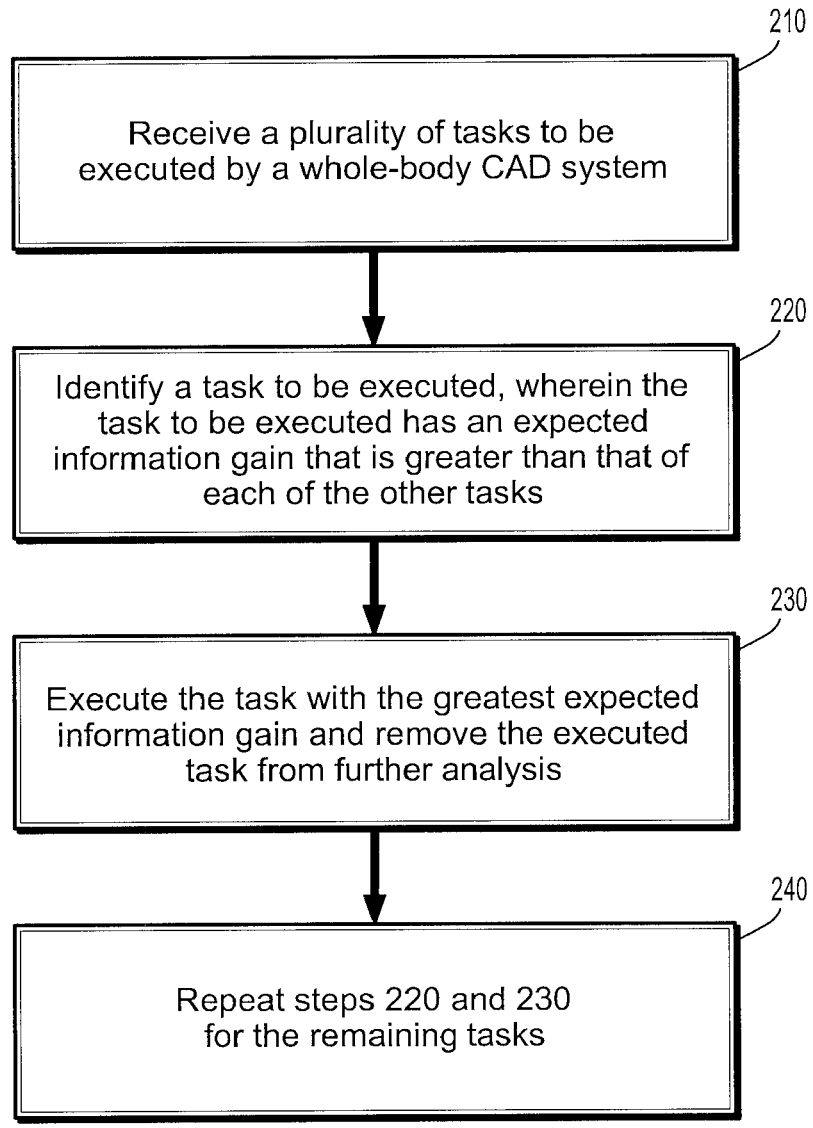
FIG. 2 is a flowchart illustrating automatically scheduling tasks in whole-body computer aided detection/diagnosis (CAD) in accordance with an exemplary embodiment of the present invention.

A brief overview of the scheduling method is shown in FIG. 2. For example, in step 210 a plurality of tasks to be executed by a whole-body CAD system are received. The tasks may include a request to identify the location of a plurality of different organs in a plurality of whole-body scans. In step 220, we identify a task to be executed, wherein the task to be executed has an expected information gain that is greater than that of each of the other tasks. In step 230, the task with the greatest expected information gain is executed and removed from further analysis. Finally, in step 240, steps 220 and 230 are repeated for the remaining tasks.

The definition of information gain, i.e., the criterion of our scheduling method, is detailed next.

2. Method

2.1 Scheduling Criterion

According to information theory (T. Cover and J. Thomas, "Elements of information theory", Wiley, 1991), the information gain is defined by the reduction of entropy. In particular, conditional entropy has been successfully employed to gauge information gain in (H. Peng, F. Long and C. Ding, "Feature selection based on mutual information: criteria of max-dependency, max-relevance, and min-redundancy", IEEE Trans. PAMI 27, pp. 1226-1238, 2005) and (X. S. Zhou, D. Comaniciu and A. Krishnan, "Conditional feature sensitivity: a unifying view on active recognition and feature selection", ICCV, 2003). Accordingly, we use conditional entropy to define our scheduling criterion.

Let us assume that $\{x_i\}$ are the variables of interest for a CAD system (e.g., the locations of the organs under study) and the variable under examination is y. Prior to the measurement process the distribution of y is $\Psi$. After the measurement, its distribution is shrinks, or changes in general, to $\Phi$. Shrink means the shrink of the support of $\Psi$ to $\Phi$. In most cases, the distribution function $\Psi$ is flatter than $\Phi$. The expected information gain, IG, after this particular measurement of y is:

$$IG_y = \sum_i \left( H(x_i | y \in \Psi) - \int_{y \in \Psi} H(x_i | y \in \Phi)p(y)dy \right) \quad (1)$$

Here we abuse the expression $y \in \Psi$ to mean "y has the support of $\Psi$" or "y has the distribution of $\Psi$". And $H(x_i|y \in \Psi)$ and $H(x_i|y \in \Phi)$ are conditional entropies defined in the following form:

$$H(x_i | y \in \Phi) = -\int_{y \in \Phi} p(y) \int_{x_i \in X_i} H(x_i | y) dx_i dy \quad (2)$$

$$= -\int_{y \in \Phi} p(y) \int_{x_i \in X_i} p(x_i | y) \log p(x_i | y) dx_i dy \quad (3)$$

In a straightforward implementation, y can be one of the variables interested by the CAD system. In this scenario, y is taken from the set $\{x_i\}$, thus the first term in Eq. (1) goes away because it becomes constant for all y. In general, however, we can have y's outside of $\{x_i\}$. Then, Eq. (1) is meaningful in its complete form.

The basic principle of our IG-based scheduling rule is that a particular measurement operation y* will be preferred over others if it delivers a maximal value for IG. The justification behind this principle is described as follows. According to Eq. (1), information gain is determined by three factors: (1) the support of y before measurement, $\Psi$, (2) the measurement uncertainty of y, $\Phi$, and (3) the dependency between y and $\{x_i\}$, $p(x_i|y)$. Indeed, it is the interplay of all these three factors that determine the speed and the accuracy of whole-body CAD. Therefore, based on the definition of IG, the speed and performance of the scheduled whole-body CAD is expected to be optimized. On the contrary, ad hoc strategies, such as "pick the most confident operation first" or "pick the task that other tasks mostly depend on", can be far from optimum.

Figure 3A:
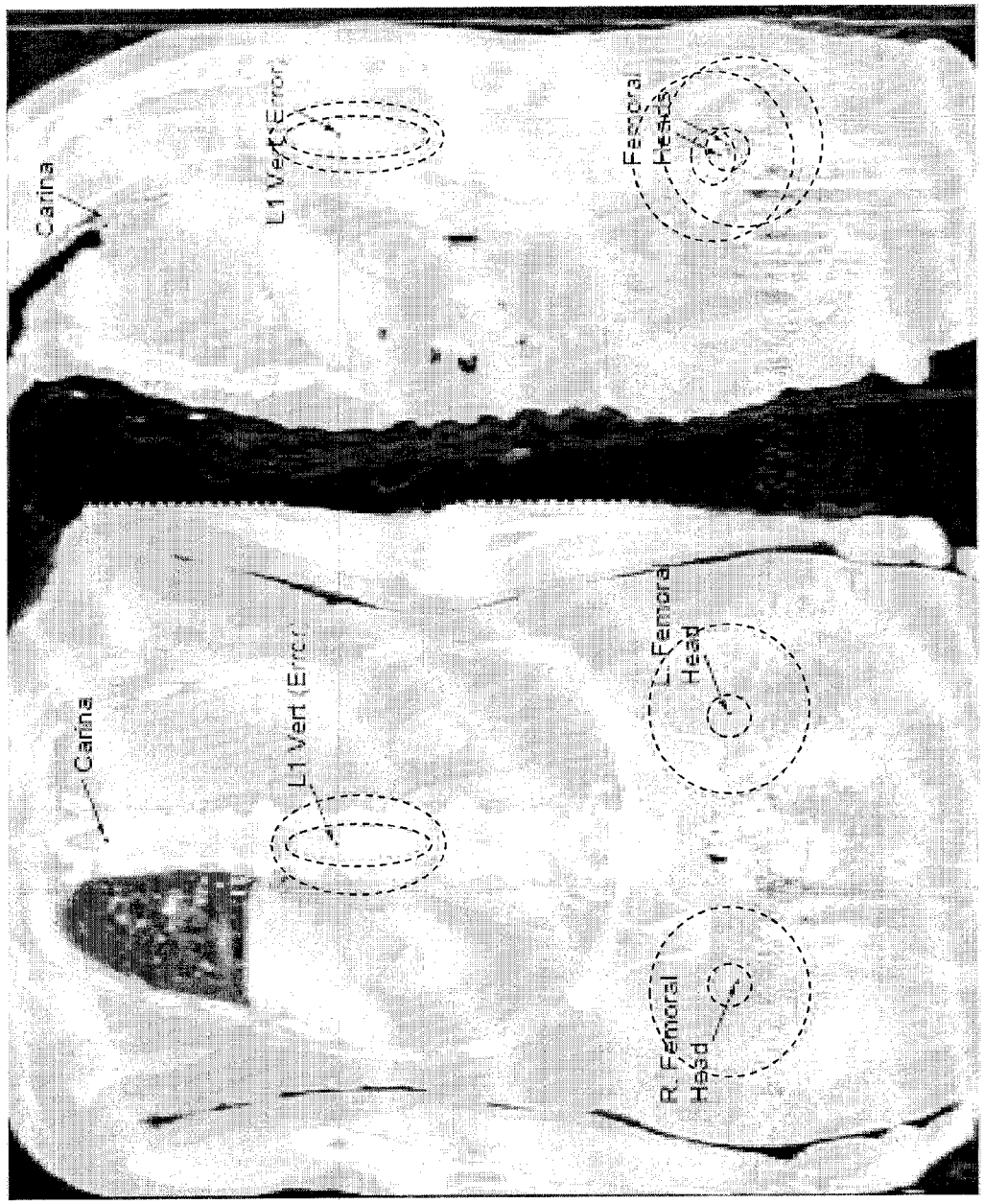
FIGS. 3A and 3B show the effectiveness of the scheduling method in-multi-organ localization in accordance with an exemplary embodiment of the present invention.
Figure 3B:
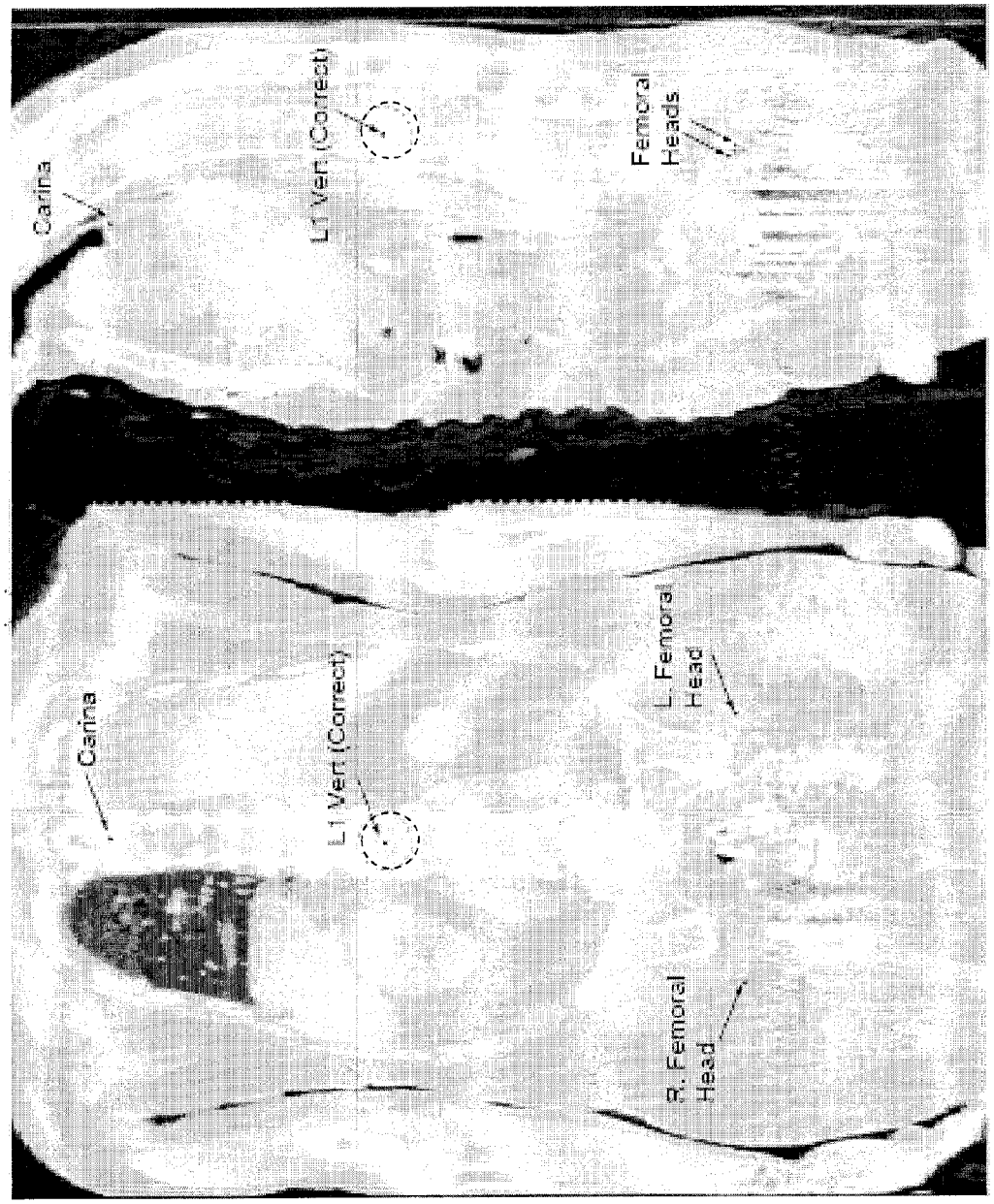

In FIG. 3 we present a rather simplified but intuitive example to show the effectiveness of the IG-based scheduling criterion. In this example, the system aims to localize four organs: carina of trachea, left femoral head, right femoral head and L1 vertebra. The dependency between different organ localization is modeled by the relative spatial location between different organs. More specifically, the positions of the localized organs are used to estimate the positions of the remaining ones to reduce the search range of other organ localizers. Let us assume the carina of the trachea has been localized. As shown in FIG. 3A, the estimated position of the L1 vertebra has the minimum support (denoted by the outer dashed ellipses). If we use an ad hoc schedule strategy that prefers the task having the minimum support, the next organ to be localized should be the L1 vertebra. However, since the neighboring anatomical structures, e.g., the L2 and the T12 vertebra, usually have similar appearance as L1, the L1 localizer is easily confused in the vertical direction (Gaussian-fitted uncertainty is denoted by the inner dashed ellipses in FIG. 3A) and get the wrong result (denoted by the "error" point in FIG. 3A). In other words, the measurement of L1 has large uncertainty, which is not expected to deliver large information gain. According to our IG-based scheduling criterion, instead, the two femoral heads that have stronger "shrink" from $\Psi$ to $\Phi$ are preferred as the next organs to be localized. (The supports of $\Psi$ to $\Phi$ in Eq. (1) are defined by the outer and inner dashed ellipses in FIG. 3A, respectively.) After localizing the two femoral heads, the support of the "unmeasured" L1 vertebra is significantly reduced (denoted by the dashed ellipses in FIG. 3B) and the localizer is able to successfully localize it (denoted by the "correct" point in FIG. 3B) without being confused by L2 or T12 vertebra.

In sum, FIG. 3A illustrates the uncertainty of organ positions after the trachea carina is localized. The outer dashed ellipses denote the uncertainty of the organ locations estimated by the trachea carina, i.e., $\Psi$ in Eq. (1). The inner dashed ellipses denote the expected uncertainty of organ localizers, i.e., $\Phi$ in Eq. (1). The "error" point denotes the falsely located L1 vertebra. FIG. 3B illustrates the uncertainty of organ positions after the trachea carina and the femoral heads are localized. The dashed ellipses denote the uncertainty of organ locations estimated by the trachea carina and femoral heads. For display purposes, the landmarks in FIGS. 3A and 3B are projected onto the same coronal/sagittal slice.

In summary, the scheduling criterion incorporates probabilistic factors, which influence the speed and accuracy of organ detection/segmentation, into a unified framework. Two intuitive principles are embodied in the formulation (1) an examination (task) with higher confidence, i.e., a stronger "shrink" from $\Psi$ to $\Phi$, tends to be schedule earlier; (2) an examination with higher dependency (predictive power) to all tasks, i.e., a strong correlation of y* over other variables (Eq. (3)) tends to be scheduled earlier.

2.2 Evaluation of Information Gain

Given the definition of IG, we use a forward sequential algorithm to schedule multiple tasks of whole-body CAD. At each step, we evaluate the IG of remaining tasks and pick the task that delivers the maximal IG as the next one to be executed. A Monte Carlo simulation method is employed to evaluate IG.

Recall the definition of information gain (Eq. (1)), the key point of IG evaluation lies in the calculation of the conditional entropy. Actually, it is trivial to calculate the conditional entropy H(x|y), given the conditional probability density function p(x|y). However, in most practical systems, it is very difficult, if not impossible, to estimate the conditional probability density function that describes the dependency between different organ detection segmentation. Instead, the dependency is usually provided by a predictive function with uncertainty:

$$x = f(y) + \epsilon, \epsilon \sim \gamma(\epsilon) \quad (4)$$

where f(.) is the predictive function, $\epsilon$ is a random variable with the probability density function $\gamma(\epsilon)$. For example, in a multi-organ localization CAD system where x and y represent the positions of two organs, f(.) becomes a position predictor of x based on its relative location to y, and $\gamma(\epsilon)$ reflects the uncertainty of this predictor.

Figure 4A:
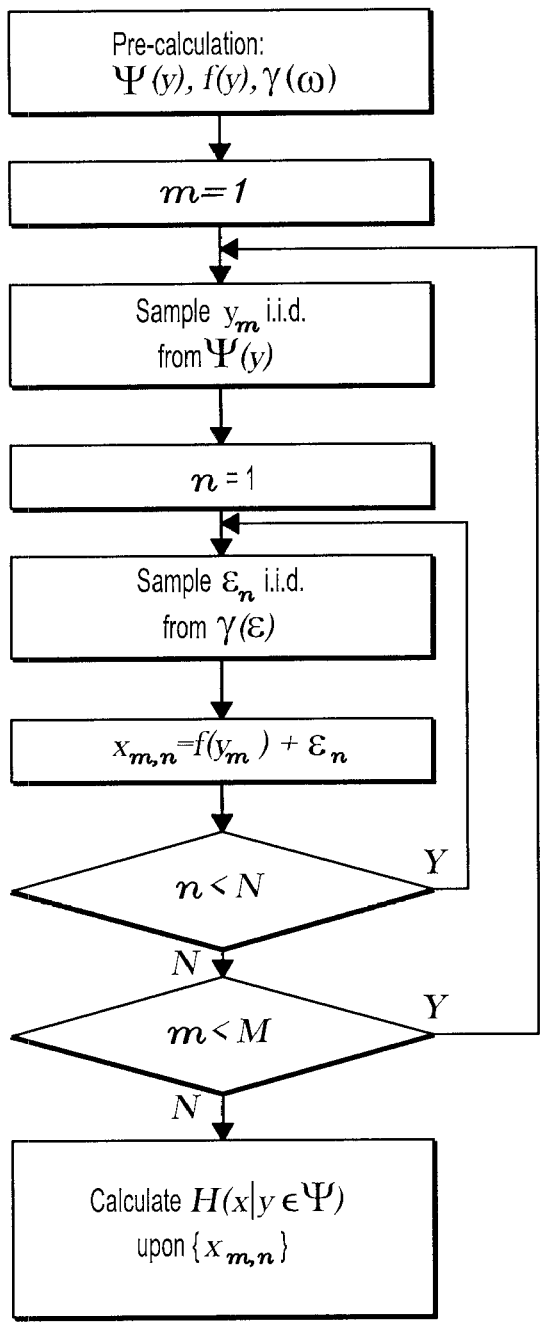
FIG. 4A is a flowchart of an algorithm to calculate $H(x|y \in \Psi)$ in accordance with an exemplary embodiment of the present invention.
Figure 4B:
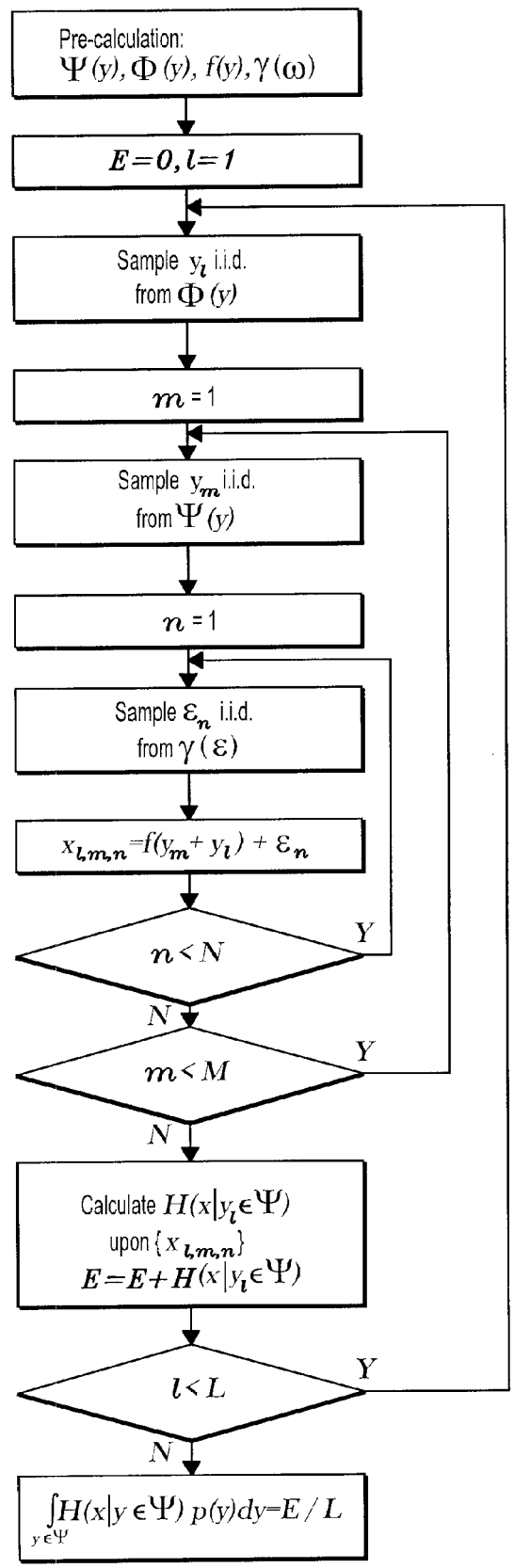
FIG. 4B is a flowchart of an algorithm to calculate $\int_{y \in \Phi} H(x|y \in \Phi)p(y)dy$ in accordance with an exemplary embodiment of the present invention.

Since f(.), $\gamma(\epsilon)$, as well as the detection/localization uncertainty, $\Psi(y)$, can be learned from a set of training data, we employ a Monte Carlo simulation method to calculate the conditional entropy as shown in FIG. 4A. In this method, the conditional entropy is directly calculated, without estimating the conditional probability density function p(x|y). Following the similar idea, the second term of Eq. (1) is calculated using the algorithm as shown in FIG. 4B.

3. Results

We validated our method on a relatively uniform task set, the localization of multiple organs in whole-body computed tomography (CT) images. While whole body CT scans are being accepted for more and more clinical applications, the localization of organs in whole-body CT becomes a tedious work for radiologists due to the vast amount of image data (more than 400 slice per scan). In accordance with an exemplary embodiment of the present invention, we designed an automatic system that aims to localize multiple organs from whole-body CT fast and accurately. In this system, each organ is localized by a generic learning-based localizer. The learning-based localizer is a three dimensional (3D) extension of Viola and Jones's detection method (P. Viola and M. J. Jones, "Robust real-time face detection", International Journal of Computer Vision 57, pp. 137-154, 2004) with expanded feature sets. The dependency between organ localization is modeled by the spatial relations between different organs. More specifically, the positions of the localized organs are used to estimate the positions of the remaining ones to reduce the search range of organ localizers. The uncertainty of the organ localizers ($\Psi(.)$, in Eq. (1)), and the spatial relations between different organs (f(.) and $\gamma(\epsilon)$ in Eq. (4)) are learned from a set of training samples. In the runtime, we always pick the organ that, upon localization, delivers the maximal expected IG as the next one to be localized.

Figure 5:
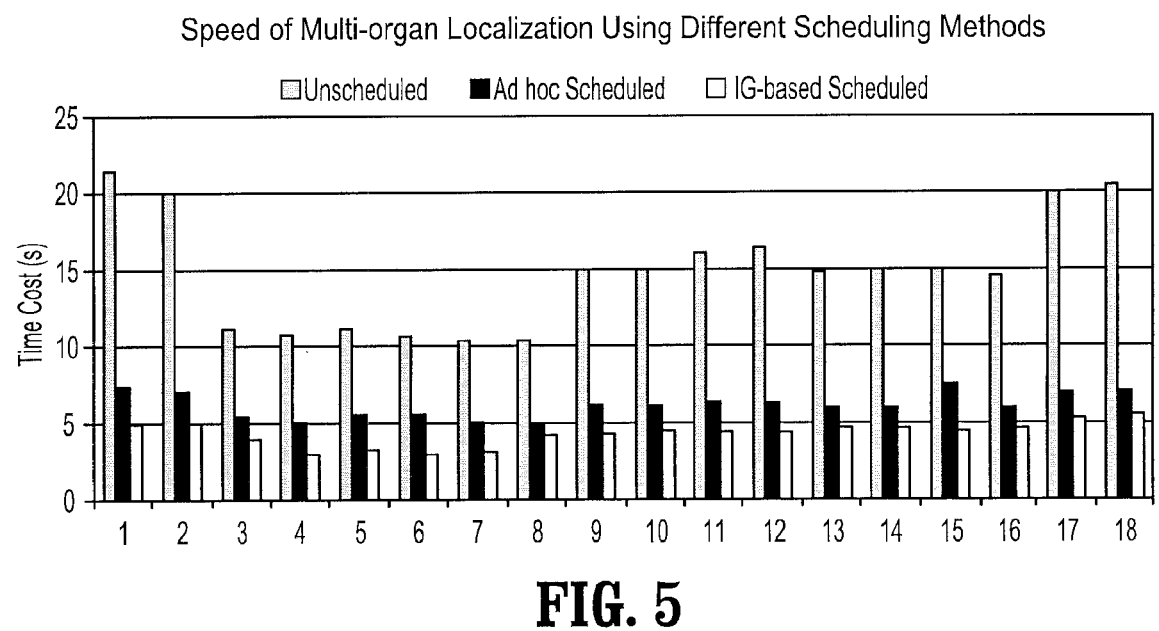
FIG. 5 is a graph illustrating a comparison of the speed of multi-organ localization using different scheduling methods.

The experiment was carried out for the localization of six organs (carina of trachea, L1 vertebra, left kidney, right kidney, left femoral head, right femoral head) from 18 whole-body CT scans. We tested the speed and the accuracy of three different scheduling methods: (1) unscheduled independent organ localization, (2) Ad hoc scheduled organ localization (the ad hoc scheduling rule prefers the organ whose location is most correlated with other organs), and (3) IG-based scheduled organ localization, in accordance with an exemplary embodiment of the present invention. Quantitative comparison results of speed and accuracy are presented in FIG. 5 and Table 1, respectively.

TABLE 1

|  | Unscheduled organ localization | | Ad hoc Scheduled organ localization | | IG-based Scheduled organ localization | |
| --- | --- | --- | --- | --- | --- | --- |
|  | Avg. Err. (mm) | Max Err. (mm) | Avg. Err. (mm) | Max Err. (mm) | Avg. Err. (mm) | Max Err. (mm) |
| Trachea Carina | 1.97 | 4.20 | 2.02 | 7.14 | 1.97 | 4.20 |
| Femoral Head | 4.47 | 10.40 | 4.67 | 11.08 | 4.60 | 9.96 |
| Kidney | 9.98 | 19.66 | 9.15 | 21.09 | 8.97 | 19.00 |
| L1 Vertebra | 5.58 | 36.00 | 5.47 | 36.85 | 3.37 | 7.03 |

Some important observations are listed as follows:
1. The organ localization using IG-based scheduling is the fastest of the three methods. It is more than three times faster than the independent organ localization method: 4.27 sec/scan vs. 14.89 sec/scan. Compared to the ad hoc scheduling method, it saves 50% of time cost: 4.27 sec/scan vs. 6.15 sec/scan.
2. Among the 18 scans that have all organs, the independent localization method did not detect "L1 vertebra" in 2 cases and "right kidney" in 1 case, while the IG-based method had no failures.
3. For organs that have distinctive appearance characteristics, e.g., trachea carina and femoral head, the three methods achieved similar localization accuracy. A reasonable explanation is that, due to the distinctive appearance, these organs can be localized accurately without the inference from other organs. Therefore, scheduled methods, which effectively narrow down the search range of organ localizers, do not bring much advantage in terms of localization accuracy.
4. For organs that have ambiguous appearance characteristics, e.g., L1 vertebra, the IG-based scheduling approach achieves more accurate localization than the other two methods.

4. Conclusions and Extensions

In this disclosure, we explored an information theoretic method to address the scheduling problem of whole-body CAD. The key idea is to schedule tasks in such an order that each operation achieves maximum expected information gain over all the tasks. More specifically, task dependency is modeled by conditional probability; the outcome of each task is assumed to be probabilistic as well; and the scheduling criterion is based on the reduction of the summed conditional entropy over all tasks. A Monte Carlo simulation method is employed to evaluate information gain without estimating the conditional probability density functions. In this way, our method is able to schedule multiple tasks in whole-body CAD very fast. Our method has two major advantages in scheduling whole-body CAD. First, the probabilistic factors that influence the speed and accuracy of whole-body CAD are incorporated in the formulation of the scheduling criterion. Second, multiple tasks are scheduled in an active way, i.e., the schedule is adaptive to the image data.

The scheduling method was validated on a multi-organ localization problem, which is important to whole-body CAD. Compared to unscheduled and ad hoc scheduling methods, our method achieved the most accurate localization with the least computational cost.

A potential extension of this work exists in two aspects. First, from an optimization perspective, the sequential decision making process might not achieve the global optimal solution. A forward-backward strategy can be applied to improve it. The basic idea is to allow tasks to be executed multiple times, i.e., a task can be fired multiple times, as long as its execution can further reduce the system uncertainty. For example, in a multi-organ localization system, femoral heads can be localized again after getting the location of the iliac bifurcation. Second, our method can have potential uses beyond whole-body CAD, since a CAD system usually consists of several tasks. For example, landmark-based segmentation methods usually start from detecting a set of landmarks along the interested organ. As the detection of each landmark can be considered a task, our method can thus be applied to improve the accuracy, robustness and efficiency of these methods.

A system in which exemplary embodiments of the present invention may be implemented will now be described with reference to FIG. 6.

Figure 6:
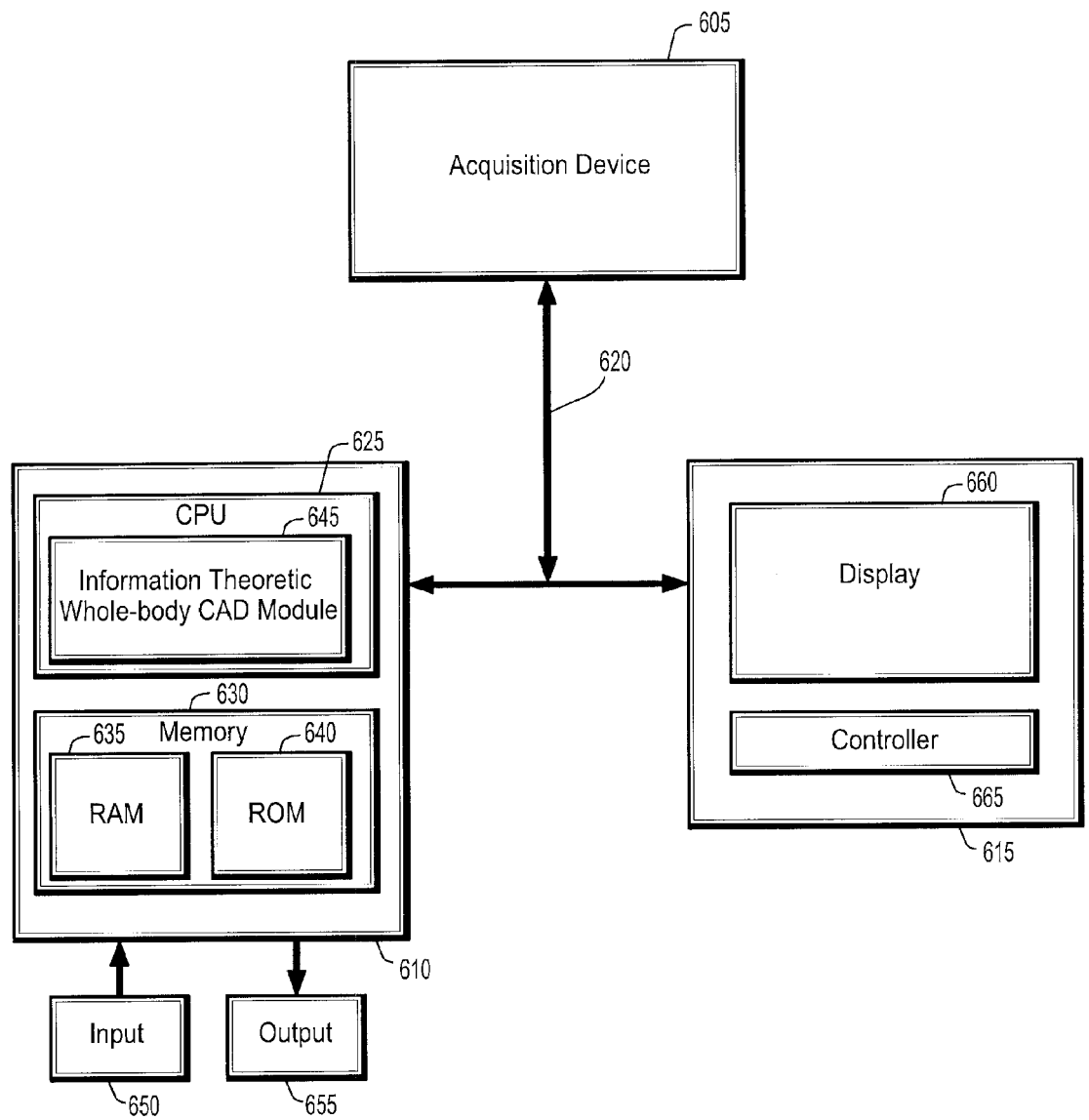
FIG. 6 is a block diagram of a system in which exemplary embodiments of the present invention may be implemented.

As shown in FIG. 6, the system includes an acquisition device 605, a personal computer (PC) 610 and an operator's console 615 connected over a wired or wireless network 620. The acquisition device 605 may be a CT, magnetic resonance (MR) or positron emission tomography (PET) scanner.

The PC 610, which may be a portable or laptop computer, a medical diagnostic imaging system or a picture archiving communications system (PACS) data management station, includes a central processing unit (CPU) 625 and a memory 630 connected to an input device 650 and an output device 655. The CPU 625 includes an information theoretic whole-body CAD module 645 that includes program code for executing methods in accordance with exemplary embodiments of the present invention.

The memory 630 includes a random access memory (RAM) 635 and a read-only memory (ROM) 640. The memory 630 can also include a database, disk drive, tape drive, etc., or a combination thereof. The RAM 635 functions as a data memory that stores data used during execution of a program in the CPU 625 and is used as a work area. The ROM 640 functions as a program memory for storing a program executed in the CPU 625. The input 650 is constituted by a keyboard, mouse, etc., and the output 655 is constituted by a liquid crystal display (LCD), cathode ray tube (CRT) display, printer, etc.

The operation of the system can be controlled from the operator's console 615, which includes a controller 665, e.g., a keyboard, and a display 660. The operator's console 615 communicates with the PC 610 and the acquisition device 605 so that image data collected by the acquisition device 605 can be rendered by the PC 610 and viewed on the display 660. The PC 610 can be configured to operate and display information provided by the acquisition device 605 absent the operator's console 615, by using, e.g., the input 650 and output 655 devices to execute certain tasks performed by the controller 665 and display 660.

The operator's console 615 may further include any suitable image rendering system/tool/application that can process digital image data of an acquired image dataset (or portion thereof) to generate and display images on the display 660. More specifically, the image rendering system may be an application that provides rendering and visualization of medical image data, and which executes on a general purpose or specific computer workstation. The PC 610 can also include the above-mentioned image rendering system tool/application.

It is understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It is also understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It is further understood that the above description is only representative of illustrative embodiments. For convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for automatically scheduling tasks in whole-body computer aided detection/diagnosis (CAD), comprising:
   receiving a plurality of statistically dependent tasks to be executed by a whole-body CAD system;
   actively scheduling the tasks by:
   (a) identifying a task to be executed, wherein the task to be executed has an expected information gain that is greater than that of the other remaining tasks, wherein the expected information gain is represented by $$IG_y = \sum_i \left( H(x_i \mid y \in \Psi) - \int_{y \in \Psi} H(x_i \mid y \in \Phi) p(y) dy \right),$$

wherein $H(x_i|y \in \Psi)$ is a conditional entropy before executing the task and $H(x_i|y \in \Phi)$ is a conditional entropy after executing the task, $x_i$ is a goal of the task, y is an outcome after executing the task, $\Psi$ is a distribution of the outcome before executing the task and $\Phi$ is a distribution of the outcome after executing the task;
   (b) executing the task with the greatest expected information gain and removing the executed task from further analysis; and
   (c) repeating steps (a) and (b) for the remaining tasks.

2. The method of claim 1, wherein the plurality of tasks comprises a plurality of organs or anatomical structures to be located in a plurality of whole-body scans.

3. The method of claim 2, wherein the whole body scans comprise computed tomography (CT), positron emission tomography (PET) or magnetic resonance (MR) scans.

4. The method of claim 1, wherein a task that has the greatest information gain includes a stronger shrink of the support from $\Psi$ to $\Phi$ than other tasks and a strong correlation of y* over $x_i$ after executing the task than other executed tasks.

5. The method of claim 1, wherein a Monte Carlo simulation method is used to calculate the conditional entropies, evaluate the expected information gain of each of the tasks and pick the task that has the greatest expected information gain as the task to be executed.

6. A system for automatically scheduling tasks in whole-body computer aided detection/diagnosis (CAD), comprising:
   a memory device for storing a program;
   a processor in communication with the memory device, the processor operative with the program to:
   receive a plurality of statistically dependent tasks to be executed by a whole-body CAD system;
   actively schedule the tasks by:
   (a) identifying a task to be executed, wherein the task to be executed has an expected information gain that is greater than that of the other remaining tasks, wherein the expected information gain is represented by $$IG_y = \sum_i \left( H(x_i \mid y \in \Psi) - \int_{y \in \Psi} H(x_i \mid y \in \Phi) p(y) dy \right),$$

wherein $H(x_i|y \in \Psi)$ is a conditional entropy before executing the task and $H(x_i|y \in \Phi)$ is a conditional entropy after executing the task, $x_i$ is a goal of the task, y is an outcome after executing the task, $\Psi$ is a distribution of the outcome before executing the task and $\Phi$ is a distribution of the outcome after executing the task;
   (b) executing the task with the greatest expected information gain and remove the executed task from further analysis; and
   (c) repeating steps (a) and (b) for the remaining tasks.

7. The system of claim 6, wherein the plurality of tasks comprises a plurality of organs or anatomical structures to be located in a plurality of whole-body scans.

8. The system of claim 7, wherein the whole body scans comprise computed tomography (CT), positron emission tomography (PET) or magnetic resonance (MR) scans.

9. The system of claim 6, wherein a task that has the greatest information gain includes a stronger shrink of the support from $\Psi$ to $\Phi$ than other tasks and a strong correlation of y* over $x_i$ after executing the task than other executed tasks.

10. The system of claim 6, wherein a Monte Carlo simulation method is used to calculate the conditional entropies, evaluate the expected information gain of each of the tasks and pick the task that has the greatest expected information gain as the task to be executed.

11. A non-transitory computer readable medium tangibly embodying a program of instructions executable by a processor to perform method steps for automatically scheduling tasks in whole-body computer aided detection/diagnosis (CAD), the method steps comprising:
receiving a plurality of statistically dependent tasks to be executed by a whole-body CAD system;
actively scheduling the tasks by:
(a) identifying a task to be executed, wherein the task to be executed has an expected information gain that is greater than that of the other remaining tasks wherein the expected information gain is represented by $$IG_y = \sum_i \left( H(x_i \mid y \in \Psi) - \int_{y \in \Psi} H(x_i \mid y \in \Phi) p(y) dy \right),$$

wherein $H(x_i|y \in \Psi)$ is a conditional entropy before executing the task and $H(x_i|y \in \Phi)$ is a conditional entropy after executing the task, $x_i$ is a goal of the task, y is an outcome after executing the task, $\Psi$ is a distribution of the outcome before executing the task and $\Phi$ is a distribution of the outcome after executing the task;

(b) executing the task with the greatest expected information gain and removing the executed task from further analysis; and
(c) repeating steps (a) and (b) for the remaining tasks.

12. The computer readable medium of claim 11, wherein the plurality of tasks comprises a plurality of organs or anatomical structures to be located in a plurality of whole-body scans.

13. The computer readable medium of claim 12, wherein the whole body scans comprise computed tomography (CT), positron emission tomography (PET) or magnetic resonance (MR) scans.

14. The computer readable medium of claim 11, wherein a task that has the greatest information gain includes a stronger shrink of the support from $\Psi$ to $\Phi$ than other tasks and a strong correlation of y* over $x_i$ after executing the task than other executed tasks.

15. The computer readable medium of claim 11, wherein a Monte Carlo simulation method is used to calculate the conditional entropies, evaluate the expected information gain of each of the tasks and pick the task that has the greatest expected information gain as the task to be executed.

* * * * *